United States Patent
Tanaka et al.

(10) Patent No.: US 10,561,384 B2
(45) Date of Patent: Feb. 18, 2020

(54) X-RAY IMAGING SYSTEM

(71) Applicant: KAWASAKI JUKOGYO KABUSHIKI KAISHA, Kobe-shi, Hyogo (JP)

(72) Inventors: Hirofumi Tanaka, Kobe (JP); Hiroaki Kitatsuji, Kobe (JP)

(73) Assignee: KAWASAKI JUKOGYO KABUSHIKI KAISHA, Kobe-shi (JP)

( * ) Notice: Subject to any disclaimer, the term of this patent is extended or adjusted under 35 U.S.C. 154(b) by 111 days.

(21) Appl. No.: 15/753,813

(22) PCT Filed: Aug. 17, 2015

(86) PCT No.: PCT/JP2015/004075
§ 371 (c)(1),
(2) Date: Feb. 20, 2018

(87) PCT Pub. No.: WO2017/029690
PCT Pub. Date: Feb. 23, 2017

(65) Prior Publication Data
US 2018/0242938 A1   Aug. 30, 2018

(51) Int. Cl.
*H05G 1/02* (2006.01)
*A61B 6/00* (2006.01)

(52) U.S. Cl.
CPC .......... *A61B 6/4452* (2013.01); *A61B 6/4429* (2013.01); *A61B 6/4458* (2013.01);
(Continued)

(58) Field of Classification Search
CPC ... A61B 6/4452; A61B 6/4458; A61B 6/4464; A61B 6/54; A61B 6/4429; A61B 6/587
See application file for complete search history.

(56) References Cited

U.S. PATENT DOCUMENTS

| 4,894,855 A | 1/1990 | Kresse |
| 2003/0091153 A1* | 5/2003 | Crain ............ A61B 6/107 378/197 |

(Continued)

FOREIGN PATENT DOCUMENTS

| JP | 2000-197627 A | 7/2000 |
| JP | 2001-218757 A | 8/2001 |
| JP | 2011-234932 A | 11/2011 |

OTHER PUBLICATIONS

Nov. 17, 2015 Search Report issued in International Patent Application No. PCT/JP2015/004075.

*Primary Examiner* — Kiho Kim
(74) *Attorney, Agent, or Firm* — Oliff PLC

(57) ABSTRACT

An X-ray imaging system takes an X-ray of an examined part of an examination subject supported by a bed. The X-ray imaging system includes: an X-ray generator that is an X-ray source; an X-ray image pickup apparatus arranged to be opposed to the X-ray generator and configured to take an X-ray having been radiated from the X-ray generator to the examination subject and passed through the examination subject; a seven-axis vertical multi-joint first robot supporting the X-ray generator; a seven-axis vertical multi-joint second robot supporting the X-ray image pickup apparatus; and a robot controller configured to control operations of the first robot and the second robot such that the X-ray generator and the X-ray image pickup apparatus move on a spherical shell centering around an isocenter C while causing the isocenter C and the examined part to substantially coincide with each other.

6 Claims, 5 Drawing Sheets

(52) U.S. Cl.
CPC .............. *A61B 6/4464* (2013.01); *A61B 6/54* (2013.01); *A61B 6/587* (2013.01)

(56) References Cited

U.S. PATENT DOCUMENTS

| | | | |
|---|---|---|---|
| 2007/0165775 A1* | 7/2007 | Graumann | A61B 6/4441 378/19 |
| 2012/0213332 A1* | 8/2012 | Dirauf | A61N 5/1081 378/62 |
| 2015/0117603 A1* | 4/2015 | Keeve | A61B 6/0407 378/62 |

* cited by examiner

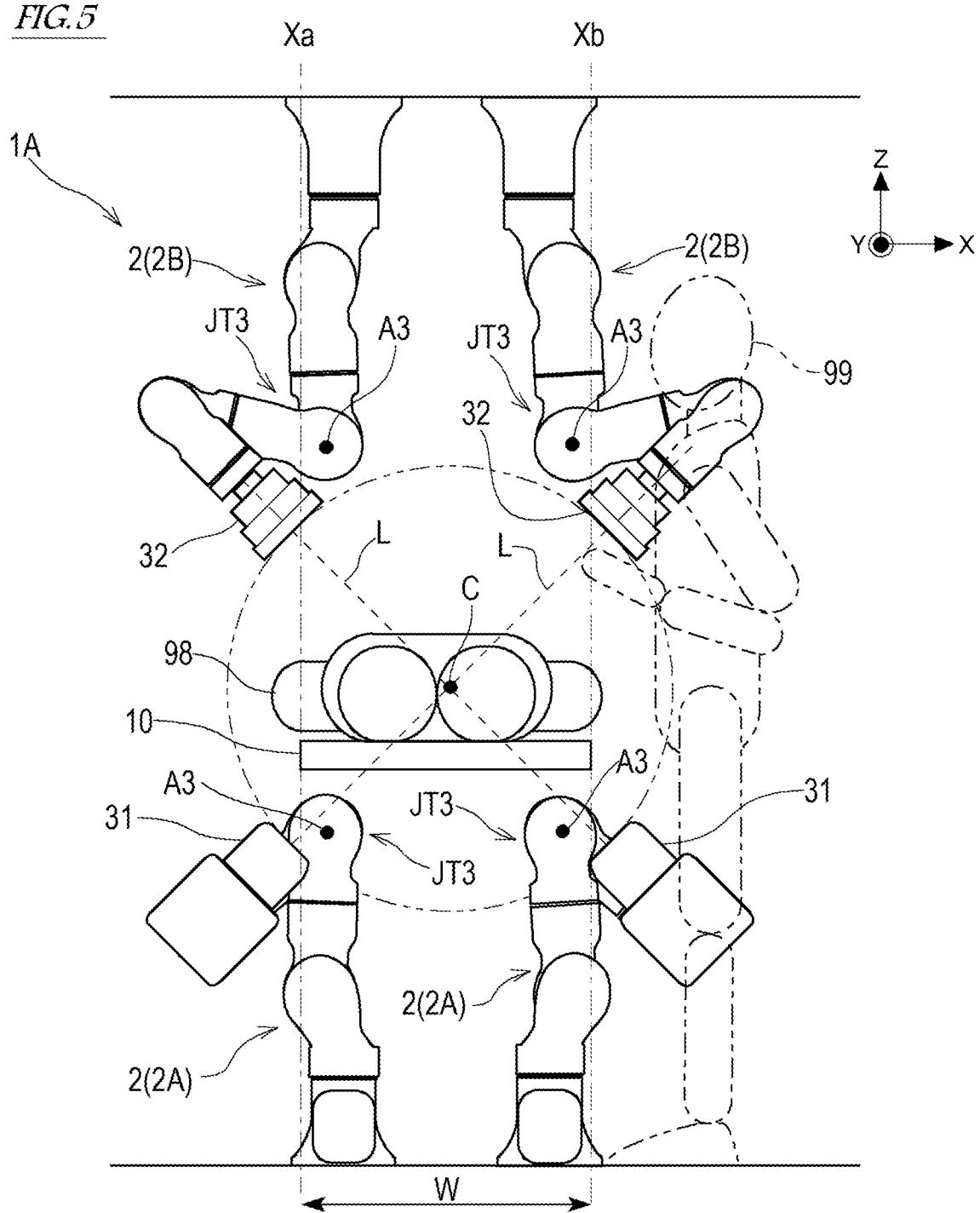

X-RAY IMAGING SYSTEM

TECHNICAL FIELD

The present invention relates to an X-ray imaging system.

BACKGROUND ART

Known as one of methods of examining human bodies using an X-ray is angiography. According to the angiography, a contrast medium is injected into a blood vessel of an examination subject, and the flow of the contrast medium is photographed by an X-ray imaging system. Thus, the shape of the blood vessel itself and the like are observed. Each of PTLs 1 and 2 discloses this type of X-ray imaging system (X-ray imaging apparatus).

The X-ray imaging system (X-ray imaging apparatus) described in PTL 1 includes: a C-type arm; a six-axis robot arm which suspends the C-type arm from a ceiling to support the C-type arm; an X-ray tube provided at one end portion of the C-type arm; and an X-ray detector provided at the other end portion of the C-type arm.

The X-ray imaging system described in PTL 2 includes: a first robot arm suspended from a ceiling; an X-ray tube supported by the first robot arm; a second robot arm provided on a floor; and an imaging apparatus supported by the second robot arm. According to this X-ray imaging system, the robot arms operate such that the X-ray tube and the imaging apparatus are moved oppositely relative to each other in two respective planes which are parallel.

CITATION LIST

Patent Literature

PTL 1: Japanese Laid-Open Patent Application Publication No. 2001-218757
PTL 2: U.S. Pat. No. 4,894,855

SUMMARY OF INVENTION

Technical Problem

In the above angiography, when a doctor injects the contrast medium into the blood vessel of the examination subject, the doctor performs work beside a bed on which the examination subject lies. For example, when performing the angiography of a heart of the examination subject, the doctor inserts a catheter into the blood vessel of a leg of the examination subject to further insert the catheter along travelling of the blood vessel to the heart. When the catheter reaches a target portion, the contrast medium is poured through the catheter. In some cases, while performing the angiography, the doctor gives a medical treatment to the examination subject at the same time.

In the angiography, the doctor and his/her assistant(s) need to perform work while paying attention to their own postures so as not to interfere with components of the X-ray imaging system. If the doctor and the assistant(s) take hard postures to avoid contact with the components of the X-ray imaging system, their work efficiency may deteriorate, and their fatigue may be promoted.

Solution to Problem

The present invention was made under these circumstances, and an X-ray imaging system according to one aspect of the present invention is an X-ray imaging system configured to take an X-ray of an examined part of an examination subject supported by a bed, the X-ray imaging system including: an X-ray source; an X-ray image pickup apparatus arranged to be opposed to the X-ray source and configured to take an X-ray having been radiated from the X-ray source to the examination subject and passed through the examination subject; a seven-axis vertical multi-joint first robot supporting the X-ray source; a seven-axis vertical multi-joint second robot supporting the X-ray image pickup apparatus; and a controller configured to control operations of the first and second robots such that the X-ray source and the X-ray image pickup apparatus move on a spherical shell centering around an isocenter while causing the isocenter and the examined part to substantially coincide with each other.

In the above X-ray imaging system, each of the first robot supporting the X-ray source and the second robot supporting the X-ray image pickup apparatus is a seven-axis robot including a redundant axis. Therefore, when the first and second robots hold the X-ray source and the X-ray image pickup apparatus and move the X-ray source and the X-ray image pickup apparatus to predetermined imaging positions, the components of the X-ray imaging system can avoid a work range of a doctor by, for example, roundabout postures of the first and second robots. With this, the work range of the doctor is secured. On this account, deterioration of work efficiency of the doctor and fatigue of the doctor, which are caused due to work by hard posture, can be expected to be suppressed or reduced.

Advantageous Effects of Invention

The present invention can cause the components of the X-ray imaging system to avoid the work range of the doctor.

BRIEF DESCRIPTION OF DRAWINGS

FIG. 5 is a modified example showing an X-ray imaging system capable of performing biplane imaging.

DESCRIPTION OF EMBODIMENTS

Figure 1:
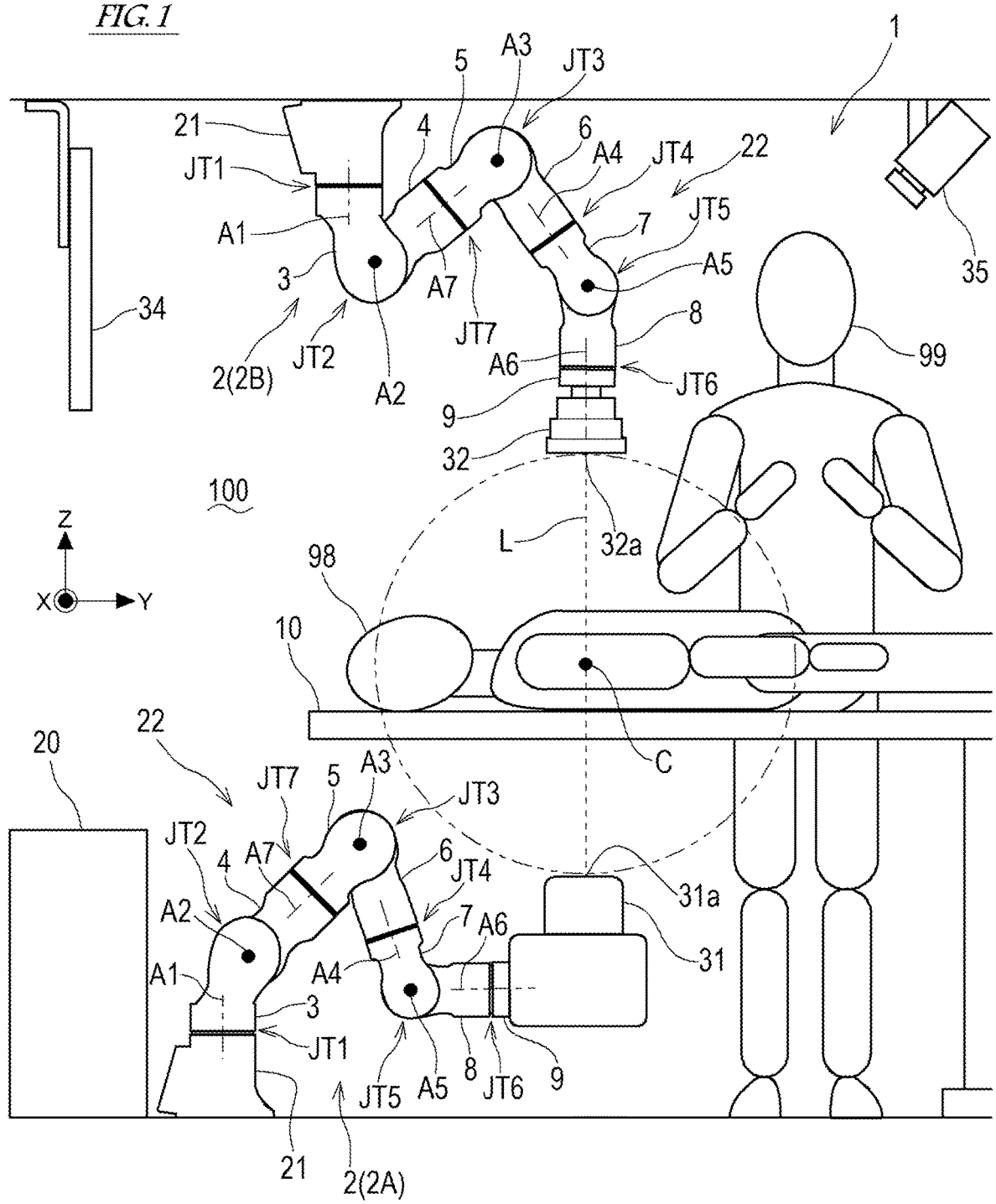
FIG. 1 is a side view showing a schematic configuration of an entire X-ray imaging system according to one embodiment of the present invention when viewed from an X direction.
Figure 2:
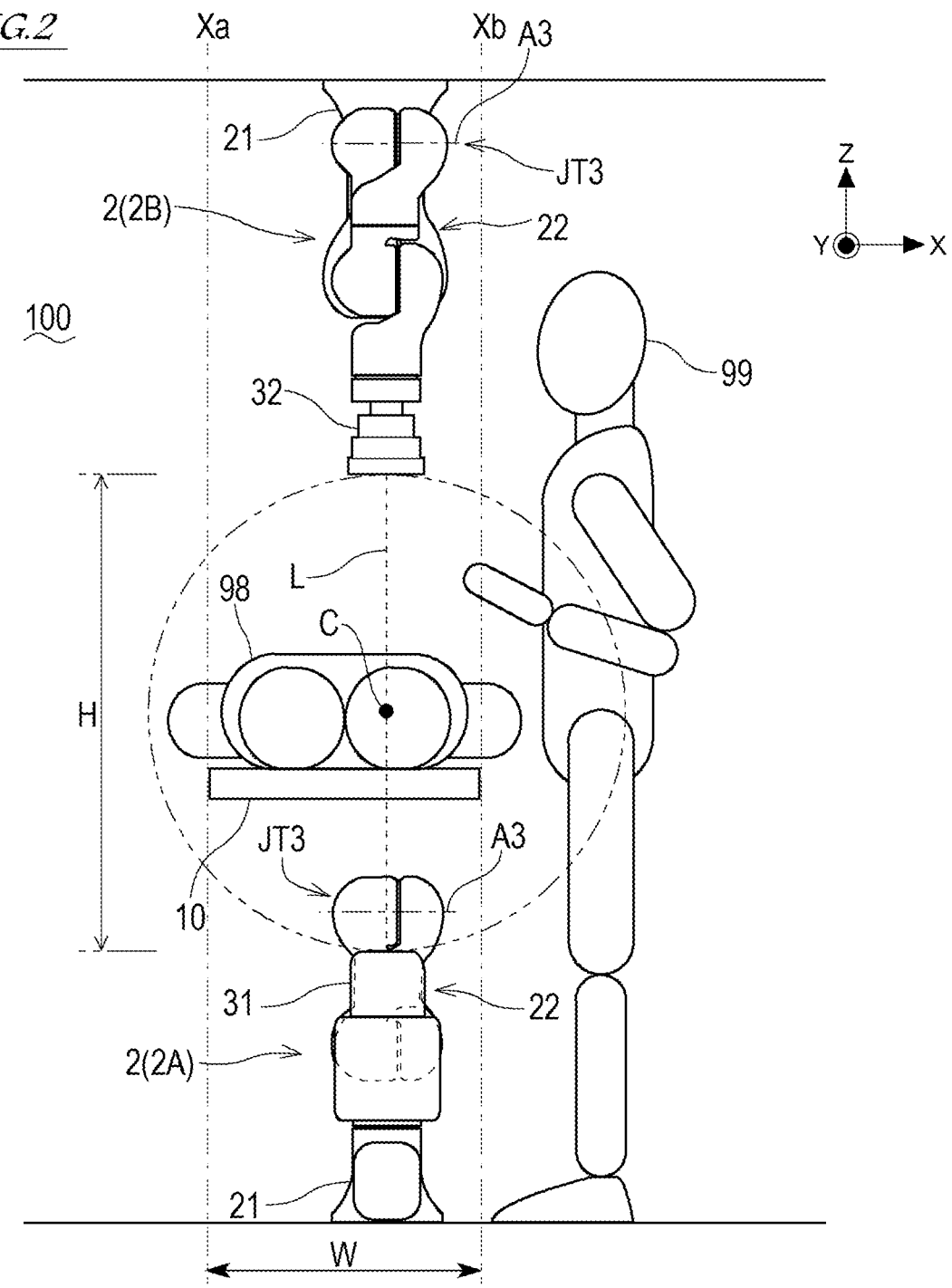
FIG. 2 is a side view showing a schematic configuration of the entire X-ray imaging system when viewed from a Y direction.
Figure 3:
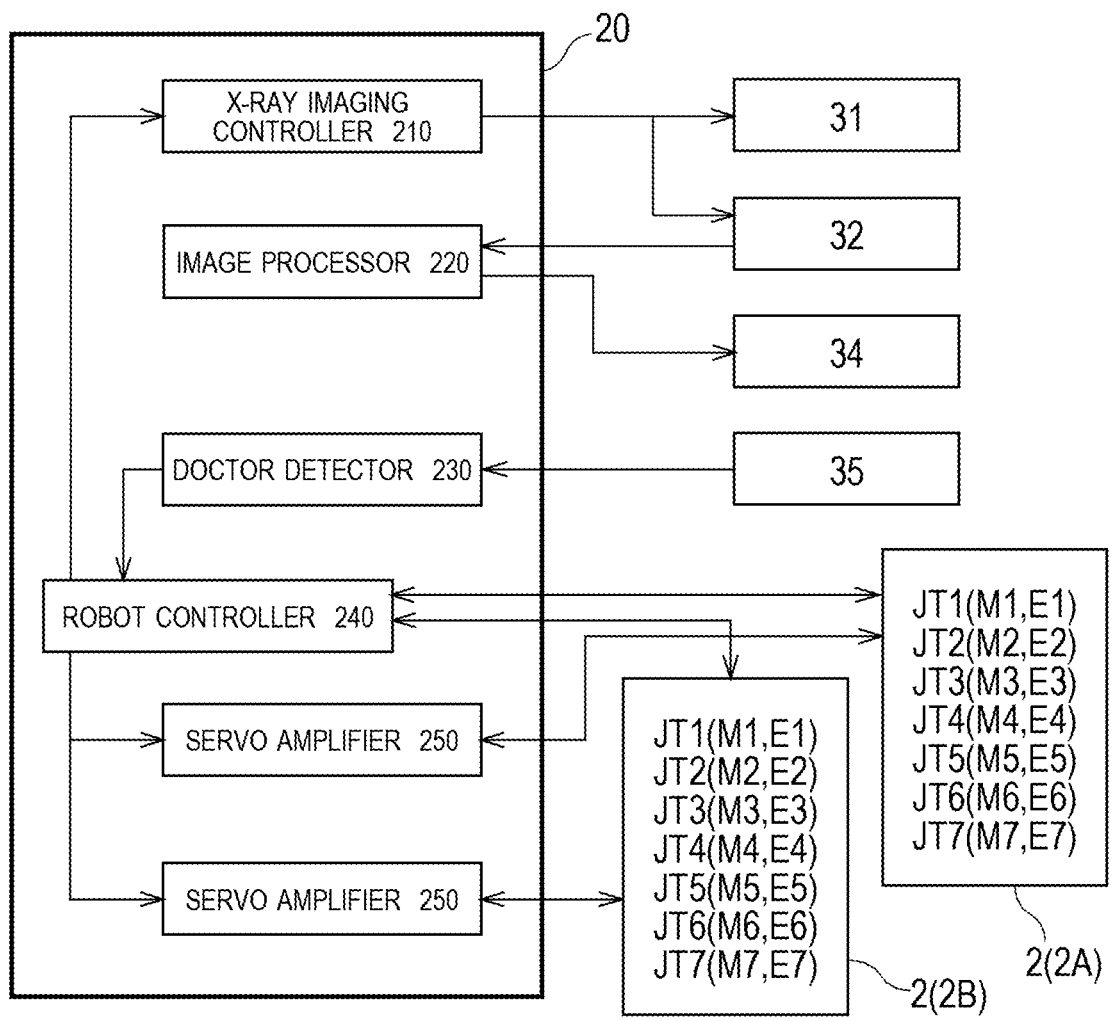
FIG. 3 is a block diagram showing a configuration of a control system of the X-ray imaging system.
Figure 4:
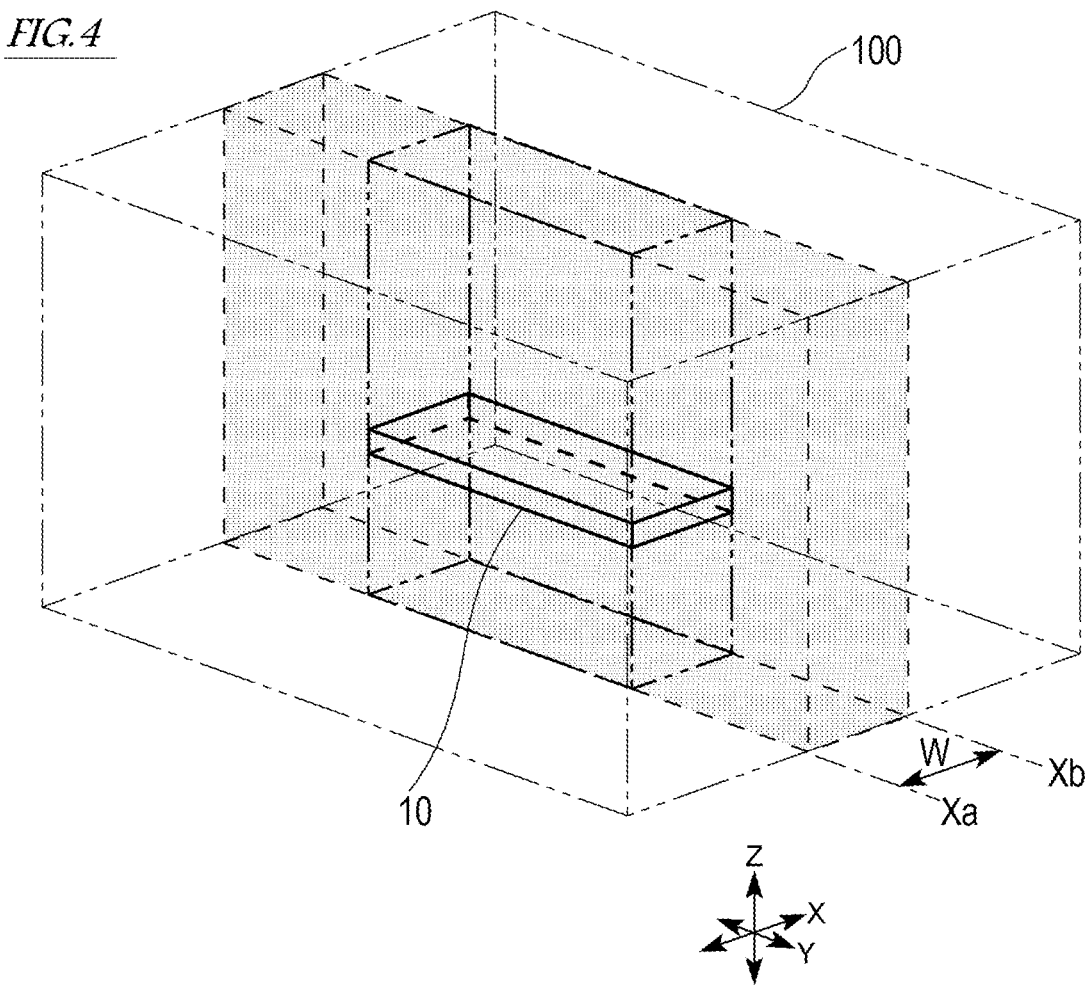
FIG. 4 is a perspective view of an examination room.

Next, an embodiment of the present invention will be explained in reference to the drawings. FIG. 1 is a side view showing a schematic configuration of an entire X-ray imaging system 1 according to one embodiment of the present invention when viewed from an X direction. FIG. 2 is a side view showing a schematic configuration of the entire X-ray imaging system 1 when viewed from a Y direction. FIG. 3 is a block diagram showing a configuration of a control system of the X-ray imaging system 1. FIG. 4 is a perspective view of an examination room 100. Hereinafter, for convenience of explanation, a paper surface depth direction in FIG. 1 is referred to as the "X direction." The X direction is a certain horizontal direction. A horizontal direction perpendicular to the X direction is referred to as the "Y direction," and a vertical direction is referred to as a "Z direction."

As shown in FIGS. 1 to 4, the X-ray imaging system 1 according to one embodiment of the present invention is constructed in the examination room 100 in which a bed 10 is provided. The bed 10 includes a length direction (long-length direction) and a width direction (short-length direction) and is arranged in the examination room 100 such that the length direction is parallel to the Y direction, and the width direction is parallel to the X direction. The bed 10 may be fixed or movable. An examination subject 98 lies on the bed 10 such that a leftward/rightward direction of the examination subject 98 is parallel to the width direction of the bed 10. A doctor 99 and his/her assistant(s) perform work regarding an examination beside the bed 10.

The X-ray imaging system 1 substantially includes: at least a pair of robots 2; an X-ray generator 31; an X-ray image pickup apparatus 32; a monitor 34; a camera 35; and a control system 20 configured to control these components. The X-ray imaging system 1 may include the above-described bed 10.

The control system 20 includes functional elements that are: an X-ray imaging controller 210 configured to control the X-ray generator 31 and the X-ray image pickup apparatus 32; an image processor 220; a doctor detector 230; a robot controller 240 configured to control the robots 2; and servo amplifiers 250. Each of the elements of the control system 20 may be, for example, a calculation control unit constituted by at least one of a microcontroller, a CPU, a MPU, a PLC, a DSP, an ASIC, and a FPGA. For example, the servo amplifier 250 may be configured such that: a CPU performs interface processing with a host calculation control unit; and a DSP performs basic calculations (position loop calculation, speed loop calculation, and current loop calculation) of the servo amplifier 250. Further, for example, each of the elements of the control system 20 may be constituted by one calculation control unit or a plurality of calculation control units which cooperate to perform distributed control. Or, a plurality of elements of the control system 20 may be constituted by one calculation control unit.

Out of the pair of robots 2, one robot 2 (2A) is fixed to a floor of the examination room 100, and the other robot 2 (2B) is fixed to a ceiling of the examination room 100. Specific configurations of the robots 2 will be described later in detail.

The X-ray generator 31 is supported by the robot 2 (2A) fixed to the floor of the examination room 100 out of the pair of robots 2. The X-ray generator 31 may be constituted by, for example, a high voltage generator, an X-ray tube configured to receive application of a high voltage to generate an X-ray, and the like.

The X-ray image pickup apparatus 32 is arranged so as to be opposed to the X-ray generator 31 across an examined part of the examination subject 98. More specifically, a radiation window 31a of the X-ray generator 31 and an image receiving surface 32a of the X-ray image pickup apparatus 32 are opposed to each other across the examined part with a predetermined focal spot-image reception distance H. The X-ray image pickup apparatus 32 is constituted by, for example, an image intensifier, an optical system, a camera, and the like (which are not shown). The X-ray image pickup apparatus 32 is supported by the robot 2 (2B) fixed to the ceiling of the examination room 100 out of the pair of robots 2.

Operations of the X-ray generator 31 and the X-ray image pickup apparatus 32 are controlled by the X-ray imaging controller 210. To be specific, the X-ray imaging controller 210 causes the X-ray generator 31 to generate the X-ray at a predetermined timing. The X-ray generated by the X-ray generator 31 is radiated from the radiation window 31a of the X-ray generator 31 toward the image receiving surface 32a of the X-ray image pickup apparatus 32. The X-ray imaging controller 210 causes the X-ray image pickup apparatus 32 to take the X-ray at a timing corresponding to the generation of the X-ray. In the X-ray image pickup apparatus 32, the X-ray having passed through the examination subject 98 is converted into an optical image, and the optical image is taken into the camera through the optical system to be converted into an image signal.

Based on the image signal received from the X-ray image pickup apparatus 32, the image processor 220 generates an image data subjected to such image processing that the doctor 99 can easily and visually recognize the examined part. Then, the image processor 220 outputs the generated image data to the monitor 34. It should be noted that the image processor 220 may be configured to, based on image signals generated by photographing from multiple directions, generate multi-slice tomographic image data or three-dimensional image data. The doctor 99 can perform examinations and medical treatments while visually recognizing an image of the examined part of the examination subject 98, the image being output to the monitor 34.

The camera 35 is provided in the examination room 100 so as to be able to photograph the doctor 99. In addition to the doctor 99, the camera 35 may photograph at least one of the examination subject 98 and the robots 2. The camera 35 is connected to the doctor detector 230, and video data (image data) obtained by the camera 35 is transmitted to the doctor detector 230. Based on this video data, the doctor detector 230 detects a work range of the doctor 99. It should be noted that the work range of the doctor 99 may include an existing range of the doctor 99, a moving range of the doctor 99, a predicted moving range of the doctor 99, and the like. Information regarding the work range of the doctor 99 detected by the doctor detector 230 is transmitted to the robot controller 240 and is utilized for operating the components of the X-ray imaging system 1 such that the components avoid the work range of the doctor 99.

The structure of the robot 2 will be explained in detail. The pair of robots 2 are substantially the same in structure as each other. Therefore, the following will explain the structure of one of the pair of robots 2 in detail, and an explanation of the other robot 2 is omitted.

The robot 2 is constituted by a base 21 and a robot arm 22. The base 21 is fixed to the ceiling or floor of the examination room 100. It should be noted that the robot 2 may be configured such that: a travelling device is included between the base 21 and the ceiling or floor of the examination room 100; and the base 21 is movable relative to the ceiling or floor of the examination room 100.

The robot arm 22 is configured by consecutively providing a swivel base 3, links 4, 5, 6, 7, and 8, and an attachment 9 in this order from a base end of the robot arm 22 toward a tip end of the robot arm 22. The swivel base 3 is supported by the base 21 so as to be turnable around a rotation axis A1. The components 3 to 9 provided consecutively from the swivel base 3 to the attachment 9 are coupled to one another so as to be rotatable relative to one another. The X-ray generator 31 (or the X-ray image pickup apparatus 32) is attached to a flange surface constituting a tip end of the attachment 9.

The robot 2 configured as above is a so-called seven-axis vertical multi joint robot including seven joints JT1 to JT7.

The robot 2 includes the six joints JT1 to JT6 defined in the same manner as a typical six-axis multi joint robot and further includes the joint JT7 for adding a redundant axis between the joints JT2 and JT3. The seven joints JT1 to JT7 include respective rotation axes A1 to A7. The seven rotation axes A1 to A7 are arranged such that rotation axes each for turning its adjacent joint and rotation axes each for swinging its adjacent joint are alternately provided from a base end of the robot 2 toward a wrist of the robot 2. It should be noted that the reference signs (JT1 to JT7 and A1 to A7) of the seven joints and the seven rotation axes are attached for convenience sake, and any reference signs may be used as long as the seven joints and the seven rotation axes are distinguishable.

In the robot 2 configured as above, a part from the rotation axis A2 to the rotation axis A3 may be referred to as an upper arm, a part from the rotation axis A3 to the rotation axis A5 may be referred to as a lower arm, a coupling portion between the upper arm and the lower arm may be referred to as an elbow, and a part from the rotation axis A5 to the tip end of the robot arm 22 may be referred to as a wrist. The rotation axes A4 to A6 are rotation axes set at the wrist. The rotation axes A1, A2, A7, and A3 are used as the rotation axes each for horizontally turning or swinging the X-ray generator 31 (or the X-ray image pickup apparatus 32) and serve as main axes of the seven-axis vertical multi joint robot.

The joints JT1 to JT7 are provided with respective servo motors M1 to M7 and respective position detectors E1 to E7. Each of the position detectors E1 to E7 is constituted by, for example, a rotary encoder. By driving the servo motors M1 to M7, the joints JT1 to JT7 rotate around the corresponding rotation axes A1 to A7. It should be noted that the servo motors M1 to M7 can be driven independently. Further, when the servo motors M1 to M7 are driven, the position detectors E1 to E7 detect rotational positions of the servo motors M1 to M7 around the rotation axes A1 to A7.

The operations of the robot 2 are controlled by the robot controller 240 and the servo amplifier 250. In the present embodiment, one servo amplifier 250 is provided for one robot 2. However, one servo amplifier 250 may be provided for a plurality of robots 2. The servo amplifier 250 performs servo control with respect to the servo motors M1 to M7 of the joints JT1 to JT7 of the robot 2 such that the tip end of the attachment 9 (i.e., the tip end of the robot arm 22) is moved along an arbitrary path to an arbitrary position and an arbitrary posture. A plurality of servo amplifiers 250 are provided so as to form servo loops individually for the servo motors M1 to M7. However, one servo amplifier 250 may collectively drive the servo motors M1 to M7.

The robot controller 240 controls the entire control system 20 including the servo amplifiers 250. The robot controller 240 is connectable to, for example, a teach pendant. An operator can use the teach pendant to perform teaching work. Based on an operation program created by the teaching work, an offline tool, etc., the robot controller 240 calculates a target position at which the X-ray generator 31 (or the X-ray image pickup apparatus 32) should be located. Further, the robot controller 240 performs inverse conversion of coordinate data of the target position, i.e., calculates joint angles $\theta 1$ to $\theta 7$. The joint angles $\theta 1$ to $\theta 7$ are necessary to: avoid interference with the doctor 99 and the predicted moving range, detected by the doctor detector 230, by the posture of the robot 2 such as roundabout of the robot 2; and move the X-ray generator 31 (or the X-ray image pickup apparatus 32) to the target position.

In the foregoing, the robot controller 240 controls the position and posture of the robot 2 such that the joint JT3 that is the fourth joint counted from the base end of the robot 2, i.e., an elbow joint is located within a width W of the bed 10. When an intersection point between the rotation axis A7 and the rotation axis A3 is defined as a reference point of the joint JT3, an "X position of the joint JT3" denotes an X position (X-coordinate) of the reference point of the joint JT3. Further, the wording "within the width W of the bed 10" denotes a three-dimensional region extending from an X position (Xa) of a right end portion of the bed 10 to an X position (Xb) of a left end portion of the bed 10 from the viewpoint of the examination subject 98 and also extending in the Y direction beyond length-direction end portions of the bed 10. In FIG. 4, the three-dimensional region corresponding to the wording "within the width W of the bed 10" in the examination room 100 is shown in gray. It should be noted that when the bed 10 is shaped to have the width W that changes in the middle of the length direction, the wording "within the width W of the bed 10" denotes a region extending from an X position (Xa) of a right end portion of a part, supporting a body portion of the examination subject 98, of the bed 10 to an X position (Xb) of a left end portion of the part of the bed 10.

The size of the bed 10 and the X positions Xa and Xb of the end portions of the bed 10 are prestored in the robot controller 240. The robot controller 240 operates the robot 2 while maintaining the X position of the joint JT3 of the robot 2 within a range from the X position Xa to the X position Xb. It is preferable that the base 21 of the robot 2 be arranged within the width W of the bed 10. This is because a control operation of locating the joint JT3 of the robot 2 within the width W of the bed 10 as above becomes easy. However, the position of the base 21 is not limited to the position within the width W of the bed 10.

Based on deviations between the joint angles $\theta 1$ to $\theta 7$ calculated as above and the rotational positions detected by the position detectors E1 to E7 when power supply is on, the robot controller 240 calculates command values of operation amounts of the servo motors M1 to M7 of the joints JT1 to JT7. Then, the robot controller 240 supplies the command values to the servo motors M1 to M7. With this, the X-ray generator 31 (or the X-ray image pickup apparatus 32) is moved to the target position.

In the X-ray imaging system 1 according to the present embodiment, two robots 2 are controlled by one robot controller 240. The robot controller 240 performs cooperative control of the pair of robots 2. By cooperative operations of the pair of robots 2, the X-ray generator 31 and the X-ray image pickup apparatus 32 move in sync with each other on a spherical shell centering around an isocenter C while causing the isocenter C and the examined part to substantially coincide with each other. At this time, the focal spot-image reception distance H between the X-ray generator 31 and the X-ray image pickup apparatus 32 is maintained at a predetermined value. The isocenter C (irradiation center) is located on an X-ray flux center line L passing through a focal spot of the X-ray generator 31 and a middle portion of the image receiving surface 32a of the X-ray image pickup apparatus 32. The pair of robots 2 can operate independently. The operations of the pair of robots 2 are synchronized with each other according to need and are not synchronized at all times.

According to the X-ray imaging system 1, the robot controller 240 controls the positions and postures of the robots 2 to move the X-ray generator 31 and the X-ray image pickup apparatus 32 to predetermined imaging positions, and the X-ray imaging controller 210 causes the X-ray generator 31 and the X-ray image pickup apparatus 32 to take the X-ray of the examined part. Thus, the X-rays are taken at a plurality of positions which are different from one another regarding an angle of the X-ray flux center line L with respect to the examined part. It should be noted that: the predetermined imaging positions and the predetermined focal spot-image reception distance H may be taught to the robot controller 240 in advance; or the X-ray imaging system 1 may be configured such that an operator can timely input the predetermined imaging positions and the predetermined focal spot-image reception distance H to the robot controller 240 through an input unit (not shown).

As explained above, the X-ray imaging system 1 of the present embodiment includes: the X-ray generator 31 (X-ray source); the X-ray image pickup apparatus 32 arranged to be opposed to the X-ray generator 31 and configured to take an X-ray having been radiated from the X-ray generator 31 to the examination subject 98 and passed through the examination subject 98; the seven-axis vertical multi-joint first robot 2 (2A) supporting the X-ray generator 31; the seven-axis vertical multi joint second robot 2 (2B) supporting the X-ray image pickup apparatus 32; and the robot controller 240 configured to control operations of the first robot 2 (2A) and the second robot 2 (2B) such that the X-ray generator 31 and the X-ray image pickup apparatus 32 move on the spherical shell centering around the isocenter C while causing the isocenter C and the examined part to substantially coincide with each other. The X-ray imaging system 1 takes the X-ray of the examined part of the examination subject 98 supported by the bed 10.

Further, in the X-ray imaging system 1 of the present embodiment, the robot controller 240 is configured to perform cooperative control of the first robot 2 and the second robot 2 such that the X-ray generator 31 the X-ray image pickup apparatus 32 move in sync with each other.

According to the X-ray imaging system 1, each of the first robot 2 (2A) supporting the X-ray generator 31 (X-ray source) and the second robot 2 (2B) supporting the X-ray image pickup apparatus 32 is a seven-axis robot including a redundant axis. Therefore, when the robots 2 hold the X-ray generator 31 and the X-ray image pickup apparatus 32 and move the X-ray generator 31 and the X-ray image pickup apparatus 32 to the predetermined imaging positions, the components of the X-ray imaging system 1 can avoid the work range of the doctor 99 by, for example, roundabout postures of the robots 2. With this, the work range of the doctor 99 is secured. On this account, deterioration of work efficiency of the doctor 99 and fatigue of the doctor 99, which are caused due to work by hard posture, can be expected to be suppressed or reduced.

Further, according to the X-ray imaging system 1, the focal spot-image reception distance H between the X-ray generator 31 and the X-ray image pickup apparatus 32 is changeable. For example, the focal spot-image reception distance H may be increased or decreased from a predetermined reference length depending on the size of the examined part and the like. Further, in accordance with the change in the focal spot-image reception distance H, at least one of an amount of X-ray radiated from the X-ray generator 31 and an angle of the X-ray radiated from the X-ray generator 31 may be changed. Further, for example, the amount of X-ray radiated from the X-ray generator 31 may be reduced in proportion to the focal spot-image reception distance H. By reducing the amount of X-ray radiated from the X-ray generator 31, a reduction in exposure of the doctor 99 and the examination subject 98 can be expected. Further, for example, the angle of the X-ray radiated from the X-ray generator 31 may be increased in proportion to the focal spot-image reception distance H.

Further, in the X-ray imaging system 1 of the present embodiment, each of the pair of robots 2 includes the rotation axes arranged such that rotation axes each for turning its adjacent joint and rotation axes each for swinging its adjacent joint are alternately provided from the base end of the robot 2 toward the wrist of the robot 2. The robot controller 240 is configured to control at least one of the pair of robots 2 such that the fourth joint JT3 (i.e., the elbow joint) counted from the base end is located within the width W of the bed 10.

As above, when the fourth joint JT3 counted from the base end of the robot 2 is located within the width W of the bed 10, the robot 2 and the X-ray generator 31 or the X-ray image pickup apparatus 32 coupled to a tip end of the robot 2 do not largely protrude in the X direction from within the width W of the bed 10. Thus, the work ranges of the doctor 99 and the assistant(s) can be secured, and oppressive feeling given to the doctor 99 and the like can be reduced.

The X-ray imaging system 1 according to the present embodiment further includes the doctor detector 230 configured to detect the work range of the doctor 99 who performs examinations. The control system 20 controls the pair of robots 2 such that the components (the X-ray generator 31, the X-ray image pickup apparatus 32, and the pair of robots 2) of the X-ray imaging system 1 avoid the work range of the doctor 99 which range is detected by the doctor detector 230.

With this, the components of the X-ray imaging system 1 move or locate so as to avoid the work range and the predicted moving range of the doctor 99. Since the work range of the doctor 99 is secured, the deterioration of the work efficiency of the doctor 99 and the fatigue of the doctor 99, which are caused due to work by hard posture, can be expected to be suppressed or reduced.

Modified Example 1

Next, Modified Example 1 of the above embodiment will be explained. In the X-ray imaging system 1 according to the above embodiment, the robot 2 is controlled such that the fourth joint JT3 counted from the base end of the robot 2 is located within the width W of the bed 10. However, in the X-ray imaging system 1 according to Modified Example 1, the robot 2 is controlled such that the second joint JT2, the third joint JT7, and the fourth joint JT3 counted from the base end of the robot 2 are located within the width W of the bed 10.

More specifically, the robot controller 240 determines the position and posture of the robot 2 such that the X position of the second joint JT2 counted from the base end and the X position of the fourth joint JT3 counted from the base end are located within a range from the X position Xa to the X position Xb. Then, the robot controller 240 transmits such command to the servo amplifier 250. When an intersection point between the rotation axis A7 and the rotation axis A2 is defined as a reference point of the joint JT2, the "X position of the joint JT2" denotes an X position (X-coordinate) of the reference point of the joint JT2. The robot 2 controlled as above transforms the robot arm 22 to move the X-ray generator 31 or the X-ray image pickup apparatus 32 to the predetermined imaging position while maintaining a state where the second joint JT2, the third joint JT7, and the fourth joint JT3 counted from the base end of the robot 2 are located within the width of the bed 10.

In the X-ray imaging system 1 according to Modified Example 1, the second joint JT2, the third joint JT7, and the fourth joint JT3 counted from the base end of the robot 2 are located within the width W of the bed 10. Therefore, the robot 2 and the X-ray generator 31 or the X-ray image pickup apparatus 32 coupled to the tip end of the robot 2 do not largely protrude in the X direction from within the width W of the bed 10. Thus, the work ranges of the doctor 99 and the assistant(s) can be secured, and the oppressive feeling given to the doctor 99 and the like can be reduced.

Modified Example 2

Next, Modified Example 2 of the above embodiment will be explained. In the X-ray imaging system 1 according to the above embodiment, the robot 2 is controlled such that the fourth joint JT3 counted from the base end of the robot 2 is located within the width W of the bed 10. However, in the X-ray imaging system 1 according to Modified Example 2, the robot 2 is controlled such that the links 4 and 5 constituting the upper arm are located within the width W of the bed 10.

More specifically, the robot controller 240 determines the position and posture of the robot 2 such that: the links 4 and 5 constituting the upper arm are regarded as a columnar body extending through the second joint JT2 and the fourth joint JT4 counted from the base end; and the X position of the columnar body is located within the range from the X position Xa to the X position Xb. Then, the robot controller 240 transmits such command to the servo amplifier 250. The robot 2 controlled as above transforms the robot arm 22 to move the X-ray generator 31 or the X-ray image pickup apparatus 32 to the predetermined imaging position while maintaining a state where the links 4 and 5 constituting the upper arm are located within the width W of the bed 10.

In the X-ray imaging system 1 according to Modified Example 2, the upper arm of the robot 2 is located within the width W of the bed 10. Therefore, the robot 2 and the X-ray generator 31 or the X-ray image pickup apparatus 32 coupled to the tip end of the robot 2 do not largely protrude in the X direction from within the width W of the bed 10. Thus, the work ranges of the doctor 99 and the assistant(s) can be secured, and the oppressive feeling given to the doctor 99 and the like can be reduced.

Modified Example 3

Next, Modified Example 3 of the above embodiment will be explained. FIG. 5 is a diagram showing a modified example of the X-ray imaging system 1 capable of performing biplane imaging. In the explanation of the present modified example, the same reference signs are used for the same or corresponding components as in the above embodiment, and a repetition of the same explanation is avoided.

The X-ray imaging system 1 according to the above embodiment includes a set of X-ray imaging units (i.e., the X-ray generator 31, the X-ray image pickup apparatus 32, and the pair of robots 2 supporting the X-ray generator 31 and the X-ray image pickup apparatus 32). However, as shown in FIG. 5, the X-ray imaging system 1 according to the present modified example includes another set of X-ray imaging units, i.e., includes two sets of X-ray imaging units. It should be noted that four robots 2 included in the X-ray imaging system 1 according to the present modified example may be controlled by one robot controller 240.

The X-ray imaging system 1 according to Modified Example 3 can simultaneously take the X-rays from two directions (this is called biplane imaging, dual plane imaging, etc.). According to this X-ray imaging system 1, an examination time can be shortened, and an amount of contrast medium can be reduced.

Especially, the X-ray imaging system 1 according to Modified Example 3 capable of performing biplane imaging has a higher effect of reducing installation spaces and operation spaces of the components than a conventional X-ray imaging system including a C-type arm. Further, since the robots 2 can operate independently, the positions and postures of the X-ray generator 31 and the X-ray image pickup apparatus 32 can be easily changed while avoiding interference between the robots 2 and interference between the robot 2 and the work range of the doctor 99.

Further, the X-ray imaging system 1 has a higher degree of freedom of the arrangement of the X-ray imaging units and is smaller than the conventional X-ray imaging system including the C-type arm. Therefore, it is easy to construct a system, such as the X-ray imaging system 1 according to Modified Example 3, including two or more sets of X-ray imaging units and capable of simultaneously taking X-rays from plural directions.

The foregoing has explained a preferred embodiment (and modified examples thereof) of the present invention, but the above configurations can be modified as below, for example.

For example, in the above embodiment and the above modified examples, one of the pair of robots 2 is fixed to the ceiling of the examination room 100, and the other robot 2 is fixed to the floor of the examination room 100. However, how to provide the pair of robots 2 is not limited to this. For example, the pair of robots 2 may be fixed to a wall of the examination room 100, or the pair of robots 2 may be fixed to the floor of the examination room 100. Or, one of the pair of robots 2 may be fixed to the ceiling or floor of the examination room 100, and the other robot 2 may be fixed to the wall of the examination room 100.

Further, in the above embodiment and the above modified examples, one robot controller 240 is provided for a plurality of robots 2. However, the robot controllers 240 may be provided for the respective robots 2, and each robot controller 240 may control the corresponding robot 2 in cooperation with the other robot controller(s) 240.

Further, in the above embodiment and the above modified examples, each of the pair of robots 2 is controlled such that the elbow joint JT3 (or the second, third, and fourth joints counted from the base end, or the upper arm) is located within the width W of the bed 10. However, only one of the pair of robots 2 may be controlled in the same manner as above.

Further, in the above embodiment and the above modified examples, the work range of the doctor 99 which range is used by the robot controller 240 when controlling the robots 2 is a range detected in such a manner that the doctor detector 230 performs image processing of the image taken by the camera 35. However, the work range of the doctor 99 is not limited to this. For example, the work range of the doctor 99 which range is detected in such a manner that an infrared thermal camera takes images of the doctor 99 and his/her surroundings and the obtained temperature distribution images are subjected to image processing may be used when controlling the robots 2. Further, for example, the work range of the doctor 99 which range is detected in such a manner that the doctor 99 carries a marker and coordinates of the marker are mapped may be used when controlling the robots 2. Further, for example, the work range of the doctor 99 which range corresponds to contents of an examination and is prestored in the robot controller 240 may be used when controlling the robots 2.

From the foregoing explanation, many modifications and other embodiments of the present invention are obvious to one skilled in the art. Therefore, the foregoing explanation should be interpreted only as an example and is provided for the purpose of teaching the best mode for carrying out the present invention to one skilled in the art. The structures and/or functional details may be substantially modified within the scope of the present invention.

REFERENCE SIGNS LIST

1 X-ray imaging system
2 robot
3 turning base
4 to 8 link
9 attachment
10 bed
20 control system
21 base
22 robot arm
31 X-ray generator (X-ray source)
32 X-ray image pickup apparatus
34 monitor
35 camera
98 examination subject
99 doctor
100 examination room
210 X-ray imaging controller
220 image processor
230 doctor detector
240 robot controller
250 servo amplifier
A1 to A7 rotation axis
C isocenter
E1 to E7 position detector
H focal spot-image reception distance
JT1 to JT7 joint
L X-ray flux center line
M1 to M7 servo motor

The invention claimed is:

1. An X-ray imaging system configured to take an X-ray of an examined part of an examination subject supported by a bed,
the X-ray imaging system comprising:
an X-ray source;
an X-ray image pickup apparatus arranged to be opposed to the X-ray source and configured to take an X-ray having been radiated from the X-ray source to the examination subject and passed through the examination subject;
a seven-axis vertical multi-joint first robot supporting the X-ray source;
a seven-axis vertical multi-joint second robot supporting the X-ray image pickup apparatus; and
a controller configured to control operations of the first and second robots such that the X-ray source and the X-ray image pickup apparatus move on a spherical shell centering around an isocenter while causing the isocenter and the examined part to substantially coincide with each other, wherein:
the controller is configured to control at leas one of the first or the second robots such that a fourth joint counted from the base end of the first or second robot is located within a width of the bed.

2. An X-ray imaging system configured to take an X-ray of an examined part of an examination subject supported by a bed, the X-ray imaging system comprising:
an X-ray source;
an X-ray image pickup apparatus arranged to be opposed to the X-ray source and configured to take an X-ray having been radiated from the X-ray source to the examination subject and passed through the examination subject;
a seven-axis vertical multi-joint first robot supporting the X-ray source;
a seven-axis vertical multi-joint second robot supporting the X-ray image pickup apparatus; and
a controller configured to control operations of the first and second robots such that the X-ray source and the X-ray image pickup apparatus move on a spherical shell centering around an isocenter while causing the isocenter and the examined part to substantially coincide with each other, wherein:
each of the first and second robots includes rotation axes arranged such that rotation axes each for turning its adjacent joint and rotation axes each for swinging its adjacent joint are alternately provided from a base end of the robot toward a wrist of the robot; and
the controller is configured to control at least one of the first or the second robots such that a fourth joint counted from the base end of the first or the second robot is located within a width of the bed.

3. The X-ray imaging system according to claim 2, wherein:
the controller is configured to control at least one of the first or the second robots such that a second, third and fourth joints counted from the base end of the first or the second robot is located within a width of the bed.

4. An X-ray imaging system configured to take an X-ray of an examined part of an examination subject supported by a bed, the X-ray imaging system comprising:
an X-ray source;
an X-ray image pickup apparatus arranged to be opposed to the X-ray source and configured to take an X-ray having been radiated from the X-ray source to the examination subject and passed through the examination subject;
a seven-axis vertical multi-joint first robot supporting the X-ray source;
a seven-axis vertical multi-joint second robot supporting the X-ray image pickup apparatus; and
a controller configured to control operations of the first and second robots such that the X-ray source and the X-ray image pickup apparatus move on a spherical shell centering around an isocenter while causing the isocenter and the examined part to substantially coincide with each other, wherein:
each of the first and second robots includes an upper arm, a lower arm, and a wrist; and
the controller is configured to control at least one of the first or the second robots such that the upper arm is located within a width of the bed.

5. An X-ray imaging system configured to take an X-ray of an examined part of an examination subject supported by a bed, the X-ray imaging system comprising:
an X-ray source;
an X-ray image pickup apparatus arranged to be opposed to the X-ray source and configured to take an X-ray having been radiated from the X-ray source to the examination subject and passed through the examination subject;

a seven-axis vertical multi-joint first robot supporting the X-ray source;

a seven-axis vertical multi-joint second robot supporting the X-ray image pickup apparatus;

a controller configured to control operations of the first and second robots such that the X-ray source and the X-ray image pickup apparatus move on a spherical shell centering around an isocenter while causing the isocenter and the examined part to substantially coincide with each other; and a doctor detector configured to detect a work range of a doctor who performs an examination, wherein the controller is configured to control the first and second robots such that the X-ray source, the X-ray image pickup apparatus, the first robot, and the second robot avoid the work range of the doctor, the work range being detected by the doctor detector.

6. An X-ray imaging system configured to take an X-ray of an examined part of an examination subject supported by a bed, the X-ray imaging system comprising:

an X-ray source;

an X-ray image pickup apparatus arranged to be opposed to the X-ray source and configured to take an X-ray having been radiated from the X-ray source to the examination subject and passed through the examination subject;

a seven-axis vertical multi-joint first robot supporting the X-ray source;

a seven-axis vertical multi-joint second robot supporting the X-ray image pickup apparatus; and a controller configured to control operations of the first and second robots such that the X-ray source and the X-ray image pickup apparatus move on a spherical shell centering around an isocenter while causing the isocenter and the examined part to substantially coincide with each other, wherein:

the X-ray imaging system comprises two or more sets of X-ray imaging units, and each of the sets of the X-ray imaging units includes the X-ray source, the X-ray image pickup apparatus, the first robot, and the second robot; and the X-ray imaging system is configured to simultaneously take X-rays from plural directions.

* * * * *